United States Patent
Gustafsson et al.

(10) Patent No.: US 6,351,924 B1
(45) Date of Patent: Mar. 5, 2002

(54) METHOD AND DEVICE FOR STERILIZING AND FILLING PACKING CONTAINERS

(75) Inventors: Per Gustafsson, Bjärred (SE); Paolo Fontanazzi, Modena (IT)

(73) Assignee: Tetra-Laval Holdings & Finance, S.A., Pully (CH)

( * ) Notice: Subject to any disclaimer, the term of this patent is extended or adjusted under 35 U.S.C. 154(b) by 0 days.

(21) Appl. No.: 09/284,659

(22) PCT Filed: Oct. 1, 1997

(86) PCT No.: PCT/EP97/05386

§ 371 Date: Apr. 16, 1999

§ 102(e) Date: Apr. 16, 1999

(87) PCT Pub. No.: WO98/17579

PCT Pub. Date: Apr. 30, 1998

(30) Foreign Application Priority Data

Oct. 18, 1996 (DE) .......................... 196 42 987

(51) Int. Cl.⁷ .............................. B65B 55/02
(52) U.S. Cl. ............... 53/425; 53/426; 53/432; 53/510
(58) Field of Search ............ 53/426, 425, 403, 53/405, 432, 510, 127, 79, 80, 269, 266.1, 271, 283, 282; 141/1, 4, 64, 70, 236, 285; 422/29, 24, 302

(56) References Cited

U.S. PATENT DOCUMENTS

| | | | | |
|---|---|---|---|---|
| 4,027,450 A | * | 6/1977 | Chiu et al. ................. | 53/110 |
| 4,140,159 A | * | 2/1979 | Domke ...................... | 141/70 |
| 5,417,255 A | * | 5/1995 | Sanfilippo et al. ........... | 53/432 |
| 5,447,007 A | * | 9/1995 | Reil et al. .................. | 53/282 |
| 5,487,253 A | * | 1/1996 | Hieltscher et al. .......... | 53/282 |
| 5,896,727 A | * | 4/1999 | Egli et al. .................. | 53/426 |
| 5,928,607 A | * | 7/1999 | Frisk ........................ | 53/425 |

FOREIGN PATENT DOCUMENTS

| | | |
|---|---|---|
| DE | 3235476 A1 | 5/1983 |
| DE | 39 30 593 A1 | 3/1989 |
| DE | 0 361 858 A1 | 4/1989 |
| DE | 0 365 867 A1 | 5/1989 |
| DE | G 92 10 753.2 | 10/1992 |
| DE | 4207829 A1 | 9/1993 |
| DE | 4305478 A1 | 8/1994 |
| DE | 4313325 A1 | 11/1994 |
| DE | 19504558 A1 | 8/1996 |
| DE | 19612322 A1 | 10/1997 |
| EP | 0 624 519 A1 | 11/1994 |
| JP | 04189727 | 7/1992 |

\* cited by examiner

*Primary Examiner*—Peter Vo
*Assistant Examiner*—Sam Tawfik
(74) *Attorney, Agent, or Firm*—Paul & Paul (57) ABSTRACT

A method is described for sterilizing, filling and closing packaging containers open on one side, in which the packaging container is exposed to a sterilizing agent during a clock-controlled transportation in a processing line through different processing stations, which is then removed with sterile hot air. Then, the packaging container is filled with sterile fluid and with a sterile closure. In order for sterilizing and also sterile filling and closure to be implemented without an expensive clean room and in a technically simple manner, it is provided according to the invention that during sterilizing the respective fluid is introduced through the center of the aperture of each individual packaging container in the respective processing station under pressure above atmospheric, approximately as far as in the area between the center and the base of the packaging container, or possibly as far as its base, wherein the fluid is deflected in the interior of the package towards the aperture and is pressed out of this such that a first part of the exiting fluid is suctioned out of the surroundings of the aperture and a second part is allowed to leave in the space around the aperture of the packaging container.

8 Claims, 5 Drawing Sheets

METHOD AND DEVICE FOR STERILIZING AND FILLING PACKING CONTAINERS

BACKGROUND OF THE INVENTION

1. Field of the Invention

The invention relates to a method for sterilizing, filling and closing packaging containers open on one side, wherein during clock-controlled transportation in a processing line through different processing stations, the packaging containers are firstly exposed to a sterilizing agent, which is subsequently removed with sterile hot air, the packaging containers are then filled with a sterile, flowable product, and are then provided with a sterile closure. The invention further relates to a device with an intermittently driven linear conveyor with container carriers arranged one behind another, at a distance apart, in a line in the direction of conveyance, which can be positioned in front of the outlet for supply lines such that the aperture of the respective packaging container comes to lie adjacent to the outlet of the respective supply line, and with a hygienic chamber at least partially surrounding the linear conveyor.

2. Brief Description of the Prior Art

There are many methods and devices for sterilizing and filling packaging containers, which have at least some of the features described hereinabove. Rotation fillers are also known, the construction and functioning of which are complex compared to linear fillers, and only have a satisfactory level of output with high capacity when there are large numbers of pieces. PET bottles, that is to say polyester bottles, for example made from polyethylene terephthalate, are processed and, for example, also sterilized in such fillers.

Other known devices, in which bottles of a similar type are sterilized, supply the bottles to a continuous conveyor with individual chambers, and the whole conveyor is arranged in a sterile chamber, which is connected by a tunnel to a sterile atmosphere for the further transportation of the then sterilized bottles.

In general a clean room or a sterile room is expensive, as locks and seals must be provided, wholly in addition to the normal measures, in order to keep such a clean room sterile, even though conveyor equipment with lubricated bearings and so forth is included. To keep such a sterile room clean, expensive measures are necessary which are undesirable in the implementation of such methods and also the construction and operation of such devices.

The object of the invention is to configure a method and a device for sterilizing of the type described in the introduction such that the sterilization and the sterile filling and closing can be carried out without an expensive clean room and in a technically simple manner.

SUMMARY OF THE INVENTION

The solution of this object with respect to the method is in that during sterilization, the respective flowable medium is introduced through the center of the aperture of each individual packaging container in the respective processing station by means of pressure above atmospheric pressure to approximately in the area between the center and base of the packaging container, or possibly as far as its base, is deflected in the interior of the container towards the aperture and is pressed out of this such that a first part of the exiting flowable medium is suctioned away from the surroundings of the aperture and a second part is allowed to leave in the space around the aperture of the packaging container. In order to explain some terms to understand the invention, one can easily imagine clock-controlled transportation, even when a continuous conveyor is driven intermittently with an approximately horizontal upper strand. The direction of conveyance of such a linear conveyor is in a processing line. In this line, one packaging container after another is conveyed in the direction of transportation, stopped, processed, conveyed further, and so forth.

Processing can be understood as pre-treating, sterilizing, removal of sterilizing agent, filling, and also closure. These are the individual processing stations which are located along a processing line. In accordance with the invention, output can be increased in that several processing lines are adjacently arranged parallel to one another, and the packaging containers standing on these lines are moved forward intermittently at the same rhythm. At right-angles to the direction of conveyance, and consequently at right-angles to the processing line, there can thus be a series of processing stations, as indeed with sterilizing, the sterilizing station can be arranged adjacent to the other ones. If, for example, eight adjacently arranged packaging containers are arranged on eight adjacently arranged parallel processing lines, these packaging containers move from one processing station to the next, whether a single or a plurality of adjacently arranged processing lines are involved.

Different flowable media can be used for sterilizing, for example gases, liquids or mixtures of these. Hot air or warm air at different temperatures, for example, can be used as gases. As sterilizing means, hydrogen peroxide ($H_2O_2$) is sprayed in liquid form, or introduced as an $H_2O_2$-air mixture or in a gaseous state. By means of the drying procedure described, any residual amount of sterilizing agent remaining in the package is removed using sterile hot air. This hot air is also such a flowable medium.

In contrast to filling, where flowable products are indeed also introduced, in the case of the invention interest is particularly in the flowable medium for sterilizing, the preparation thereof, and also the removal of any residues after introduction of the sterilizing means. In a preferred embodiment, the flowable media are at least partially gaseous substances for sterilizing, and sterile hot air for preparation and/or drying.

According to the invention, the aperture of the packaging container to be sterilized is placed in front of a stream of flowable medium in each individual processing station, which medium is introduced through the center of the container aperture under low pressure. In this way the gas located in the container is pressed out, wherein increasingly more flowable medium is pressed in through the center of the aperture into the container, as the flowable medium is at a higher pressure than atmospheric pressure because the packaging container to be processed is not only open but is also in the atmosphere. Flowable medium introduced into the aperture therefore penetrates approximately as far as the area between the center and the base, preferably as far as the base of the packaging container, and is then deflected by the walls of the container, to again flow towards the aperture. As the inflow is very much focused through the center of the opening, the outflow after the deflection towards the aperture is non-central, preferably along the internal walls of the packaging container, as far as the aperture. The flowable medium is pressed out of said aperture as a result of the pressure being above atmospheric pressure. This occurs at the same time as new flowable medium is continuously pressed into the interior through the center of the aperture. In order for the pressing out to be supported, a part of the exiting flowable medium is suctioned away from the surroundings of the aperture, and another part which is not affected by this suctioning power, and does not need to be affected, flows laterally into the space around the aperture of the packaging container.

It has been shown that in this way, no expensive clean rooms with locks, seals and the like are required. Nevertheless, by pressing out the flowable medium concerned, for example the sterilizing agent, contamination with germs of the area of the aperture, both inside and outside, is avoided, as the surfaces in the area of the aperture of the packaging container are continuously swept by the respective flowable medium. Means for directing such a flowable medium stream or a patterns of a flow stream can technically be produced with moderate expenditure, as will be proposed hereinafter. The sterilizing and filling of packaging containers in accordance with the method according to the invention is thus also technically simple to implement.

It is advantageous during sterilizing that the flowable medium leaving and being suctioned from the aperture of the packaging container surrounds the narrowly focused stream of the flowable medium being supplied in an approximately cylindrical manner and, after leaving the aperture in part, expands radially outwards. These are the measures by which fresh flowable medium can be introduced centrally through the aperture in the packaging container while simultaneously this flowable medium can flow out non-centrally after sweeping the container walls outside this inflow. In the packaging container, by means of the pressure of flowable medium being above atmospheric pressure and developing due to the inflow, there is a continuous pressure differential between the interior of the container aperture and the space around it, so that the flowable medium either spreads radially outwards or is suctioned up or away in the manner described hereinabove.

It is useful and advantageous that by means of the invention, simplifications are obtained inter alia to the extent that neither the packaging container nor any filling pipes are moved in and/or out.

It has been proven advantageous when, according to the invention, the packaging container, set up with its aperture facing upwards, is transported approximately horizontally. Then, after sterilizing and drying, the containers can be filled straight away in one of the processing stations located in a processing line, as liquids must be introduced into a package from above, at least an angle from above. A further rotation or discharging of the packaging containers is in this way avoided.

In a further advantageous embodiment of the invention, before the introduction of sterilizing agent into the packaging container, hot air is introduced to pre-warm it. In this way excessive condensation of a, for example gaseous, sterilizing agent introduced is avoided. The subsequent drying for removing condensed residues of sterilizing agent is simplified in this way.

It is thus also advantageous when, in accordance with the invention, hydrogen peroxide ($H_2O_2$) is used as the sterilizing agent, and preferably the packaging container has the form of a bottle.

By means of the flow pattern described, centrally into the aperture of the packaging container, and after sweeping of the internal surface of its walls, and flowing out in the area of the periphery outside the center of the aperture, towards the aperture, gaseous flowable medium is continuously blown out into the space surrounding the container aperture, with the result that the space around the processing stations, and where appropriate along the entire processing line, is exposed to pressure above atmospheric pressure of the flowable medium. If this entire space around the linear conveyor is now enclosed by a pipe-like housing, a hygienic chamber is obtained in the manner of an open high pressure chamber from which, at the front and rear (at the two opposite ends of the pipe), gas streams slowly flow away to the outside into the atmosphere. In this way, although a sterile space is not provided around the respective packaging containers, nevertheless the concentration of germs in this hygienic chamber is so low that in these conditions the flow pattern with the gases flowing out of the aperture of each packaging container makes possible a satisfactory sterilization of the packaging container.

With respect to the device, the object is solved according to the invention in that the aperture of each individual packaging container can be positioned in front of the outlet of a supply line and at the outlet of the respective supply line an inlet nozzle surrounded by an annular gap connected to suctioning means is fitted, and the pressure in the supply line is greater than the surrounding pressure. It must be ensured that the aperture of the respective packaging container into which the flowable medium concerned has to be introduced comes to lie adjacent to the outlet of the respective supply line. With an aperture arranged facing upwards, and a bottle standing upright, the outlet must, for example, not come to lie above said bottle at too great a distance from the upper edge of the aperture. In this case the flow pattern described can take place as a stream of flowable medium can be pressed through the inlet nozzle into the center of the packaging container. This is also possible when the packaging container lies laterally or also when the packaging container has to be arranged with its aperture approximately downwards. In this case, the aperture is conveyed over the outlet of the respective supply line, and the same conditions of introduction are produced.

The teaching of the invention provides that a supply line is not provided for a plurality of packaging containers at the same time, but instead the aperture of each individual packaging container comes in front of the outlet of a supply line. In other words, in this way in each processing station the number and position of the outlets of the supply lines equals the number of packaging containers to be processed. The sterilizing conditions according to this invention can therefore be set up, using simple means, not only for a single processing line but also for a large number of processing lines arranged adjacently parallel to one another. With regard to supply lines, a distributor could be provided for several processing stations which are all to be operated simultaneously, from which would again lead off as many outlets as the number of packages to be conveyed. In accordance with the invention, on the respective outlet of the supply line (this is now substituted for a distributer) an inlet nozzle is fitted which presses the flowable medium centrally into the aperture and which is surrounded by an annular gap behind which suction means are arranged in the direction of flow, for example a suction space which is connected to suction lines or drain lines. When now, outside the central supply stream of flowable medium, flowable medium flows cylindrically out of the aperture of the packaging container, the diameter of the annular gap is advantageously dimensioned such that the flowable medium is suctioned approximately radially towards the inside. In other words, the diameter of the annular gap is preferably smaller than the internal diameter of the aperture of the packaging container. Certainly not all of the gas or flowable medium which leaves the aperture of the packaging container will be suctioned by the annular gap and transported away, but instead there remains an amount of flowable medium which flows away radially outwards into the space around the aperture, as there, the pressure is lower than in the packaging container or in the aperture thereof. This flowing away is ensured in that the pressure in the supply line is greater than the surrounding pressure.

The flowing away from the space around the packaging container allows the provision of an open high pressure chamber, when it is further provided according to the invention that the linear conveyor is surrounded by a pipe or tunnel shaped hygienic chamber open at opposite ends. The cross-section of this chamber can be different, for example rectangular. At the open ends of this chamber a small quantity of flowable medium flows away out into the atmosphere. The desired flow pattern is obtained when it is provided, according to the invention, that a greater volume of flowable medium is blown in through the inlet nozzle in the packaging container than is suctioned through the annular gap.

In order to facilitate the narrowly focused injection of the flowable medium through the centrally arranged inlet nozzle, it can project out of the bottle preferably by a certain distance of, for example 0–20 mm, preferably between 5 mm and 10 mm outside the annular gap. This surface projecting furthest towards the aperture of the packaging container must be kept at a distance of at least several millimeters away in normal operation, apart from a short period of sealing for producing the pressure above atmospheric pressure, as in this way the packaging container can be moved freely under the inlet nozzles and the whole supply means.

It is also advantageous when in the direction of conveyance, two drying stations are connected following on from the sterilizing station. It has been shown that with some high capacity machines, the arrangement of three drying stations following the sterilizing station is useful. One supply line with one distributor with three outlets is sufficient for these three drying stations. Where appropriate suitable multiplications can be undertaken.

At least one sheet metal wall can be arranged in the direction of conveyance on each container carrier, and this sheet metal wall can be raised to the height of the aperture of the packaging container. By means of these sheet metal walls, which circulate with the linear conveyor, the air flowing out, for example enriched with $H_2O_2$, can be prevented from flowing too fast from the open-ended hygienic chamber. However, even without such sheet metal walls it has been shown that the packaging container itself represents a sufficient resistance to the flowable medium flowing out.

Further advantages, features and possibilities for application of the present invention will be evident from the following description of preferred embodiments with reference to the attached drawings.

DETAILED DESCRIPTION OF THE DRAWINGS

Figure 1:
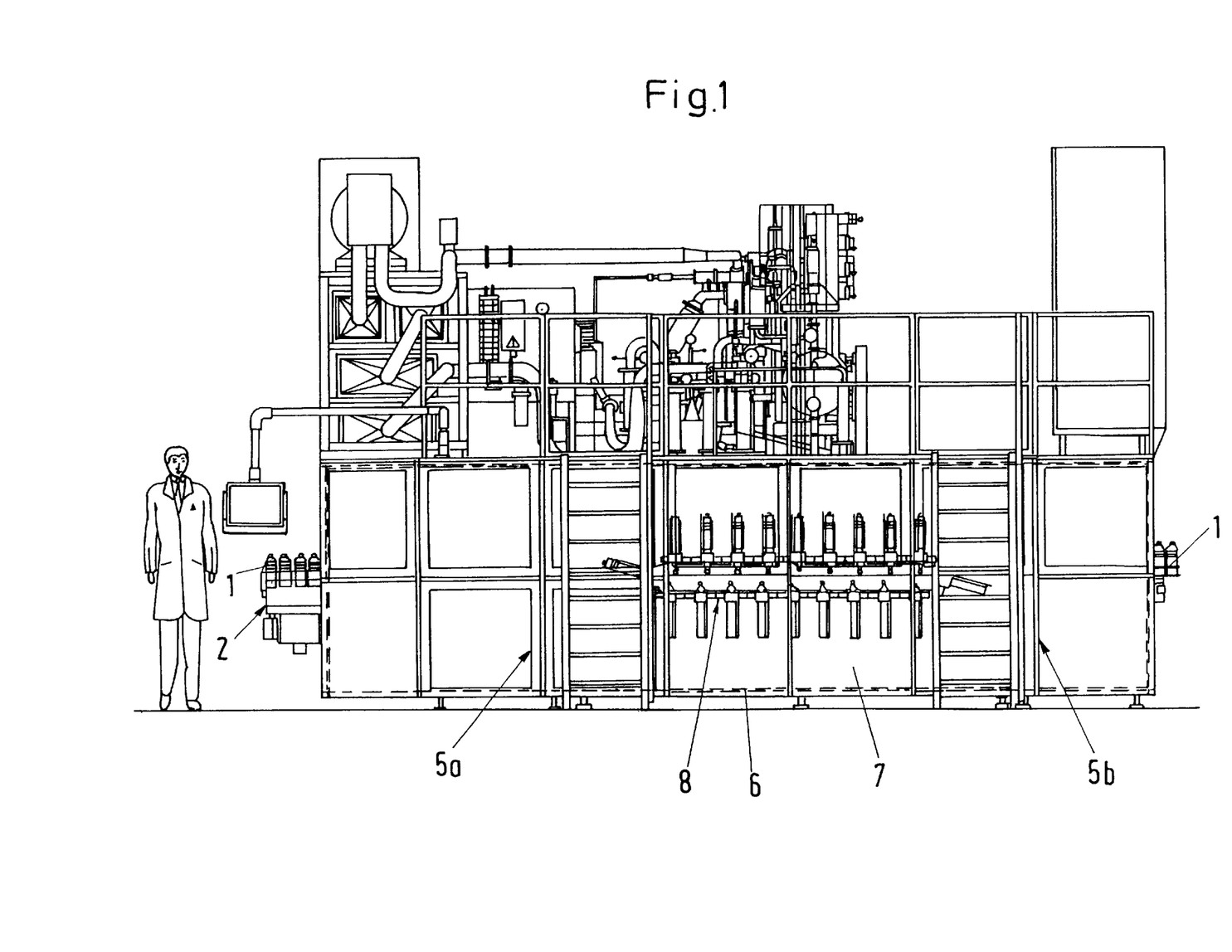
FIG. 1 is a lateral view of a sterilizing, filling and closing machine for packaging containers in the form of PET bottles.
Figure 2:
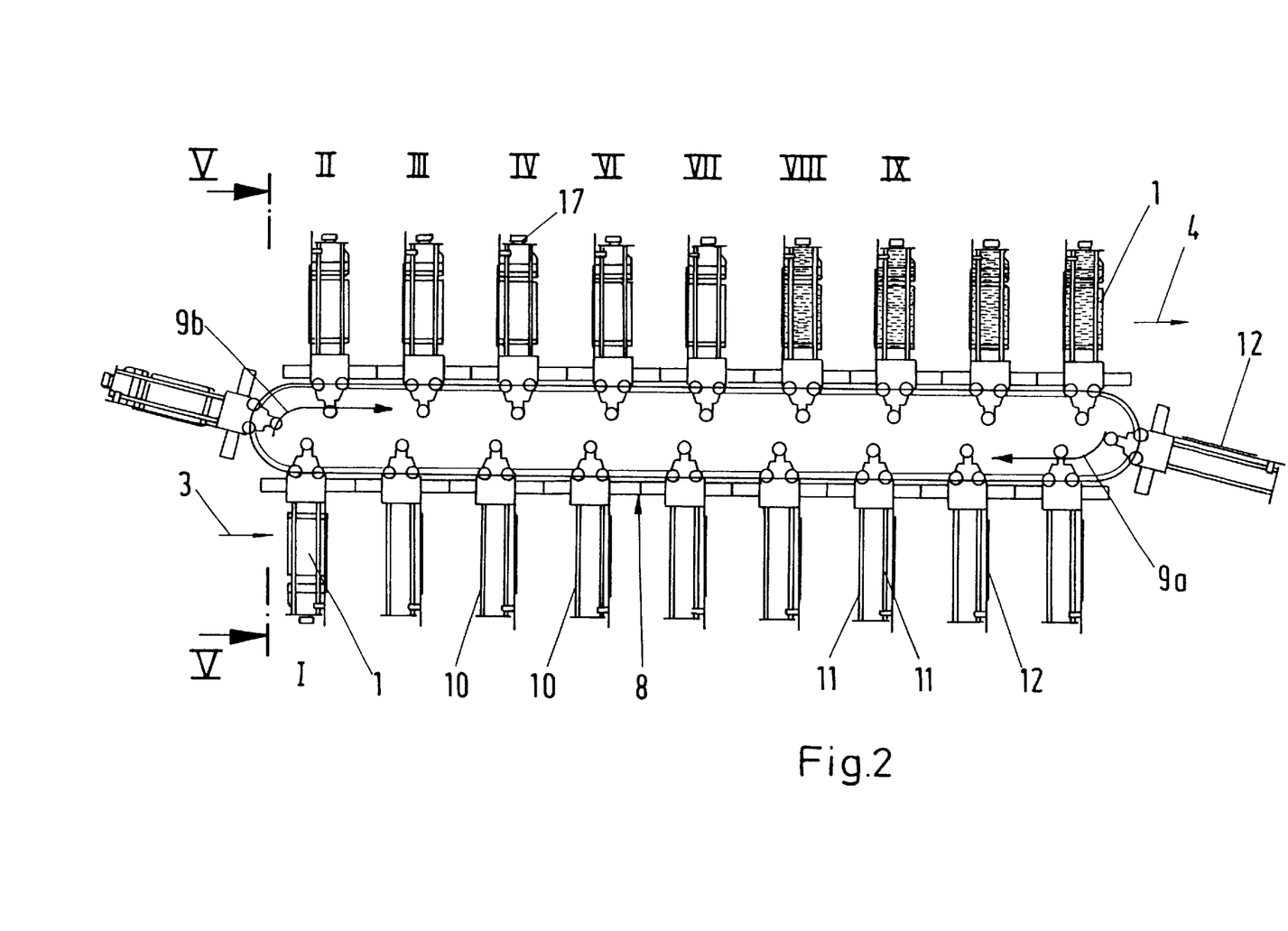
FIG. 2, schematically shown, is a continuous conveyor with a horizontally running upper strand, as can be seen behind the external walls of the lower part of the machine in FIG. 1.

Packaging containers 1 in the form of PET bottles are to be sterilized, filled and closed with the machine as a whole referenced 1. On the left-hand side shown in FIG. 1, there is located a conveyor means 2, with the aid of which containers 1 are conveyed in the direction of the arrow 3 (FIG. 2). At the upstream right-hand end of FIG. 2, the arrow 4 indicates the direction of discharge of completed and filled containers 1, the further transportation, repacking and the like of which is provided at the right-hand end of the machine in FIG. 1. FIG. 1 shows that also at the left-hand end 5a and at the opposite right-hand end 5b, an open rectangular pipe 6 which forms a hygienic chamber 7, that is to say the space in which an intermittently driven linear conveyor (continuous band) 8 is contained. The walls of the rectangular pipe 6 for forming the hygienic chamber 7 can also be seen in FIG. 5. It will be understood that the hygienic chamber can also be formed from other means, for example a downwardly open bell. While the arrow 9a arranged at the bottom right of FIG. 2 indicates the direction of transport of the lower strand of the linear conveyor 8, the direction of transport of the upper strand is shown by the arrow 9b arranged on the left in FIG. 2. The packaging container 1 is loaded according to FIG. 2 into the container carrier 10 at the bottom left in position I. This is conveyed on the linear conveyor 8 by means of rollers and supports not described in more detail, and is provided with radially projecting retaining rods 11 and also a shielding plate 12 which is located on the trailing end of the respective container carrier 10 and extends over the entire height thereof.

Figure 5:
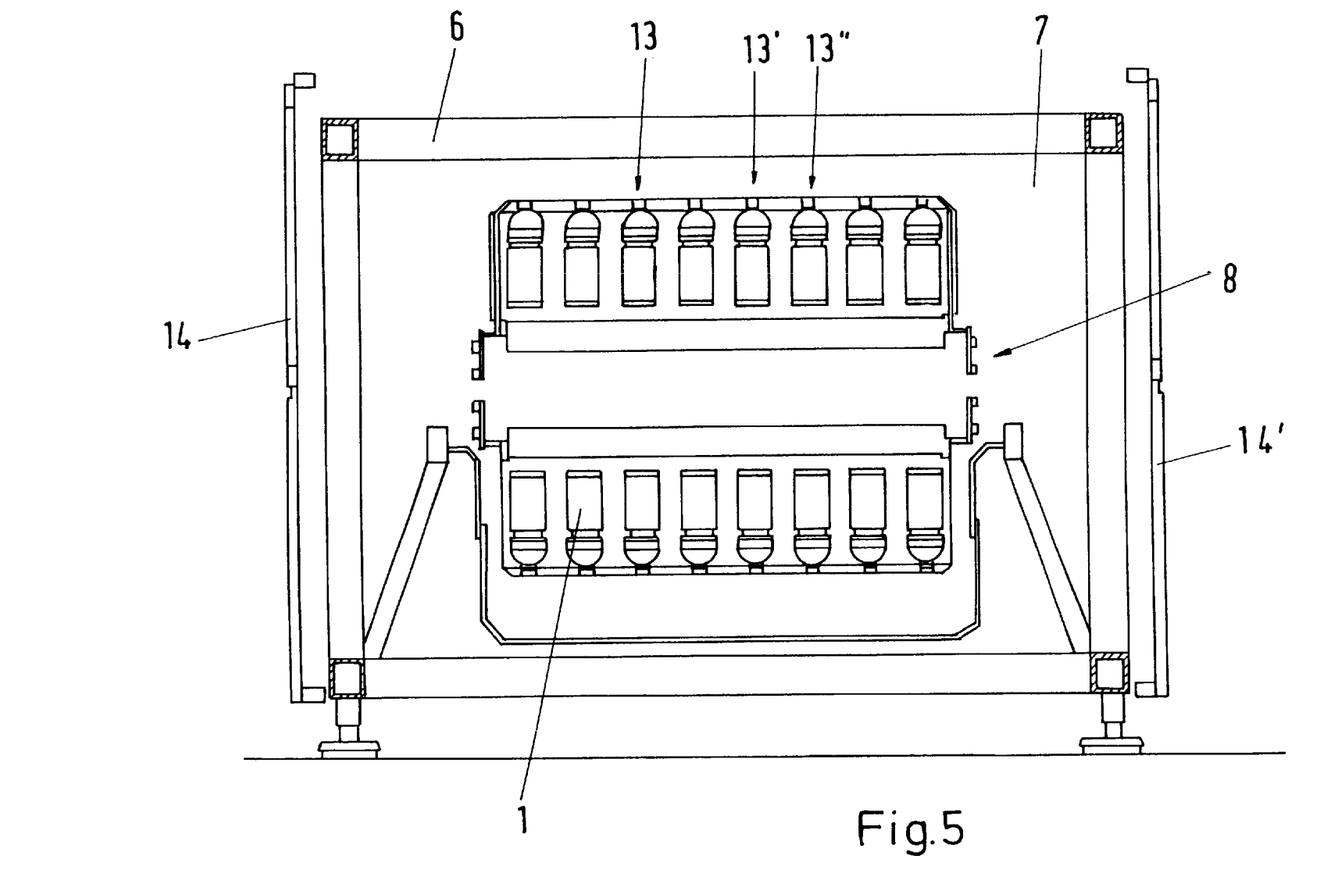
FIG. 5 is a schematic and simplified end view of the hygienic chamber along the line V—V of FIG. 2.

After loading of the container carrier 10 standing in position I with a packaging container 1, the linear conveyor 8 proceeds clockwise upwards according to the arrow 9b and then arrives in position II for the first processing step (pre-heating) as described. In the direction of transport, following this processing station II in a processing line 13 and respectively 13' and respectively 13", there are the processing stations III, IV, VI, (V is omitted because of the sectional view), VII, VIII and IX. The series of these processing stations II–IX thus represents a processing line 13 and respectively 13' and respectively 13", in which the packaging containers 1 are moved from left to right in the direction of transport in FIGS. 1, 2 and 3. It is evident from the representation in FIG. 5, according to the sectional view V—V, that there is not just one, but instead eight processing lines, so eight packaging containers 1 stand in each processing station II–IX, each of which will be subjected to the respective processing. In FIG. 5 one views the furthest forward processing station II and also the upper strand in the direction of its movement 9b (direction viewed). It is evident how one processing line 13 is arranged adjacent to the others 13', 13", and so forth. The holders for the linear conveyor 8 are not shown in more detail in FIG. 5 as any skilled person can correspondingly configure a continuous conveyor. It is evident, however, how the rectangular pipe 6, open at the front and rear, which forms the hygienic chamber 7, surrounds the entire linear conveyor 8 and is covered externally along its long sides by housing walls 14, 14' which can be seen in FIG. 1.

In FIG. 1, in the upper area of the machine there are located the units for conditioning and conveying the flowable medium such as, for example, hot air, hydrogen peroxide ($H_2O_2$), liquid foodstuffs (milk) and the like. These units are not described here in more detail, as they are 
known. It will only be shown here how the necessary flowable medium can be supplied and removed for sterilizing and maintaining cleanliness.

In this respect, FIG. 2 describes in position II the preheating, in the following position II of the processing line 13 in the direction of transport 4, 9b, the spraying in of $H_2O_2$, in position IV the first drying, in positions VI and VII the second and third dryings, in position VIII the filling, and in position IX the closure. After the further clocked conveying of the filled and closed packaging container 1, it is discharged in the direction of the arrow 4, without the subsequent movements and processes being further represented or described.

Figure 3:
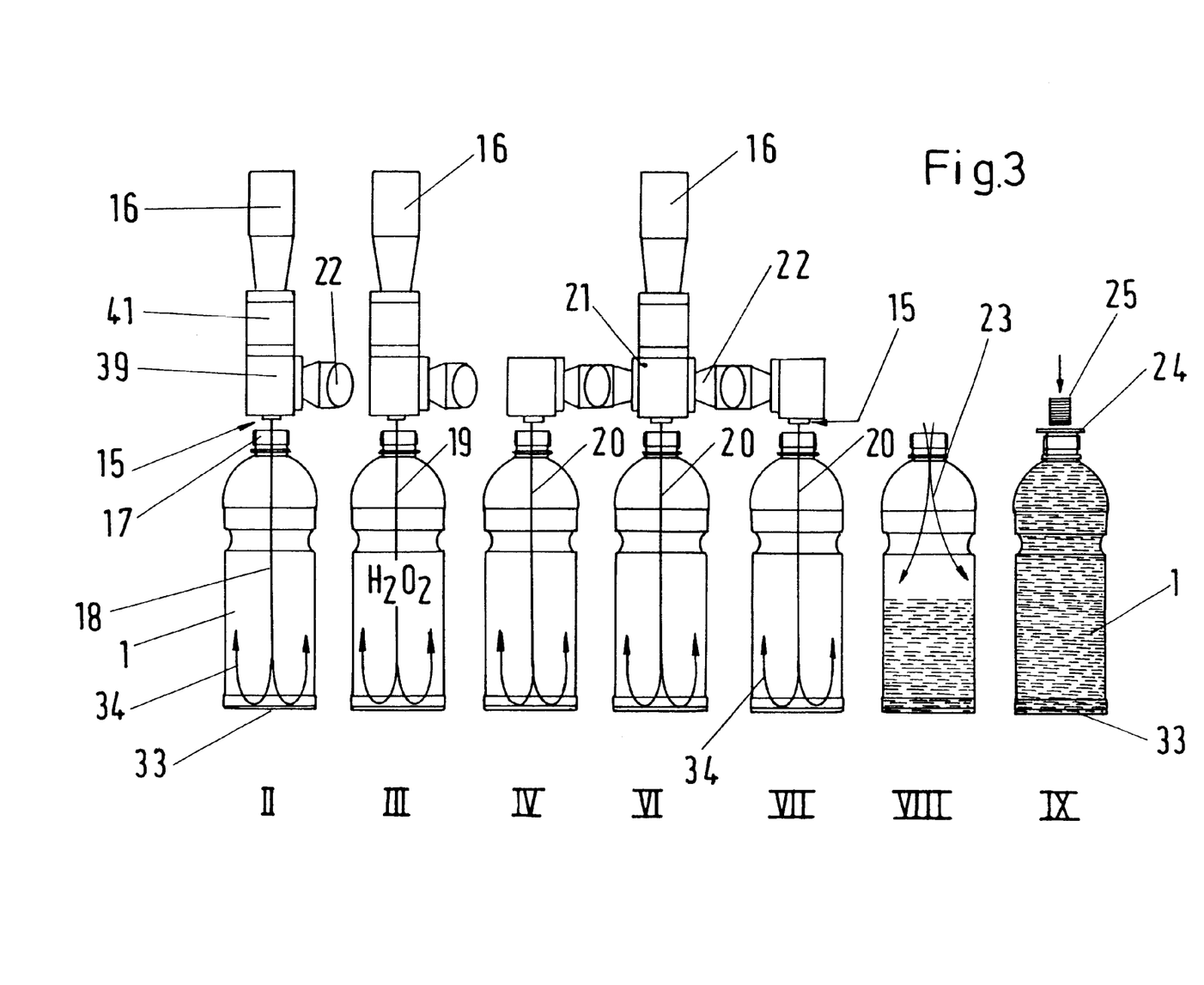
FIG. 3, for explanation of the invention, schematically condensed and enlarged, is a part of a processing line with the most important processing stations.

In FIG. 3 the processing stations II to IX are again shown, enlarged and without the linear conveyor 8, and without container carriers 10, in order to better explain the course of the method.

The individual packaging containers 1 and their container carriers 10 which are not shown can be positioned in front of the outlet 15 of supply lines 16, so that the aperture 17 of the respective packaging container 1 comes to lie adjacent to the outlet 15 of the respective supply line 16, and indeed under it, as the packaging containers 1 are always set up with their aperture facing upwards, and are transported approximately horizontally in the direction of conveyance 4, 9b.

According to FIG. 3, in position II pre-warming takes place by means of hot air 18, in position III $H_2O_2$ is blown in the form of a stream of gas 19, and in positions IV, VI and VII drying takes place, in order to remove any remaining sterilizing medium with certainty. This drying is again carried out in each case with a stream of hot air 20, which is supplied via a common supply line 16, and conducted further to the side via the distributor 21. Adjacent to every outlet 15 there is located a venting line 22, the further connections of which, for removal via suction means, are not shown. After position VII, in which the last processing, that is to say the last step in preparation of the packaging container 1, is undertaken, namely the last drying by means of hot air 20, in position VIII the filling with flowable medium takes place, which in FIG. 3 is shown in the form of the stream of flowable medium 23 (milk). The grey hatching in position VIII of FIG. 3 shows that the packaging container 1 is already half filled.

After intermittent further progression of the linear conveyor 8 into the position IX, the packaging container 1 according to FIG. 3 is clearly completely filled and will now be closed in a sterile manner, as is shown schematically by means of a sealing plate 24 and screw cover 25.

Figure 4:
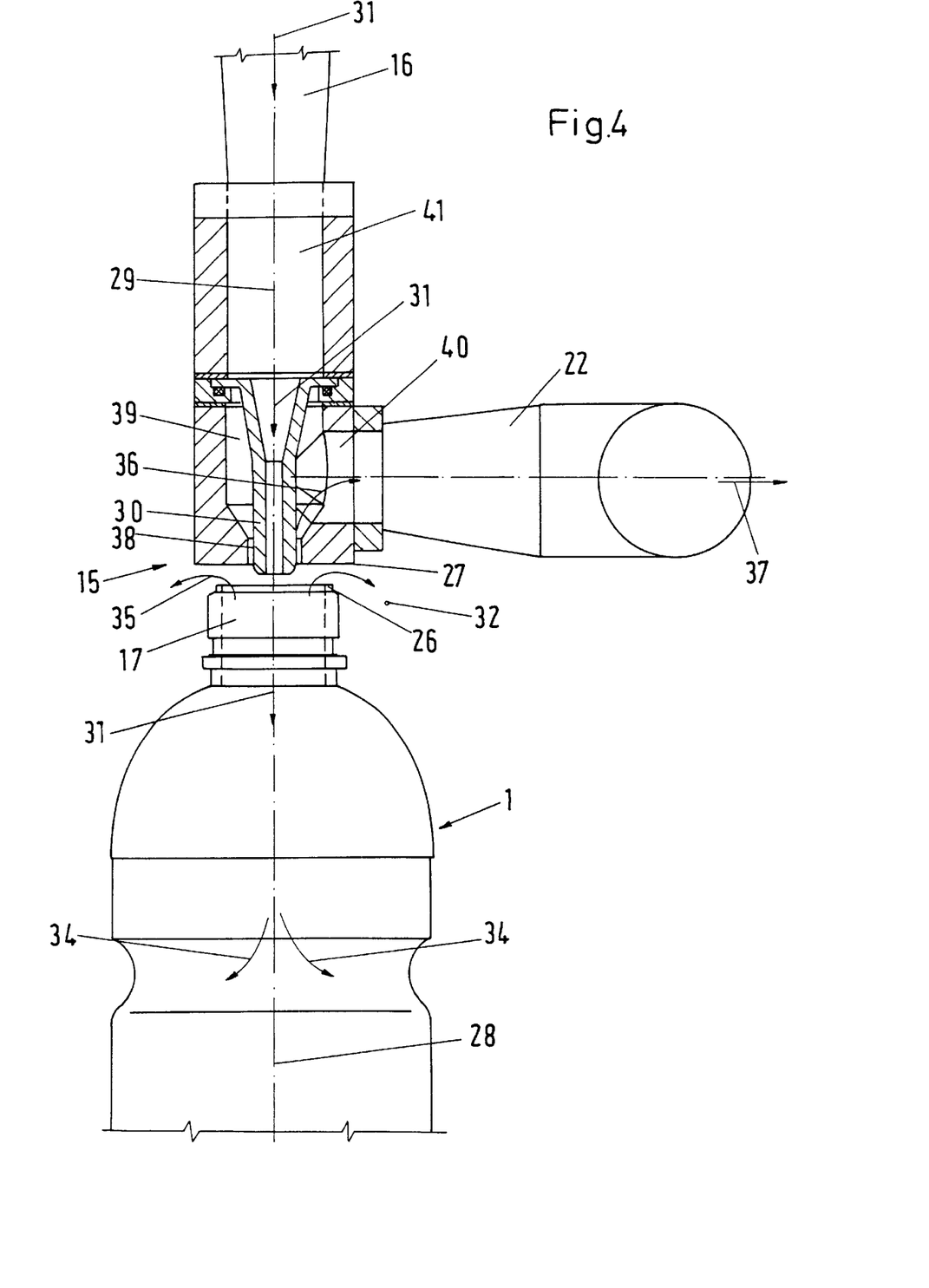
FIG. 4, greatly enlarged and partially in section, is a supply line with outlet and annular gap.

In FIG. 4 a position, for example position III, is reproduced greatly enlarged in detail and for the purpose of explanation. The aperture 17 arranged at the top on the packaging container 1 is placed in front of the outlet 15 of the supply line 16. The upper edge 26 of the aperture 17 is located at a distance of 0–20 mm, preferably between 5 and 10 mm, below an annular, planar surface 27 which should be thought of as parallel to those planes which extend from the edge 26 of the container aperture 17. In ideal circumstances, the aperture 17 is located centrally over the outlet 15, the broken central longitudinal line 28 of the packaging container is aligned with and in line with the central longitudinal line 29 of the supply line 16. The center of the outlet 15 is formed by an inlet nozzle 30, through which the respective flowable medium is introduced in the direction of the arrow 31 centrally in a preferably tightly focused stream downwards into the aperture 17 of the container 1. The flowable medium in the supply line 16 is at a pressure above atmospheric pressure, of 0.5 to 2 bar, preferably between 0.7 and 1.5 bar. Around the aperture 17 is the space, generally labelled 32, in which atmospheric pressure prevails at a distance away from the packaging container 1. The gases (or liquids when $H_2O_2$ is introduced, for example in a liquid state) flowing in along the central line 29, 31 through the center of the aperture 17 of the container 1, reach approximately as far as the area between the center and the base 33 of the packaging container. In the interior, two curved arrows 34 show how, inside the container 1, the flowable medium is deflected towards the outside and lastly is conveyed upwards again, back to the aperture 17. FIG. 3 the flowable medium stream 34 deflected on the base can be seen in positions II to VII, with the result that the flowable medium flowing upwards surrounds, in the manner of a cylinder, the narrowly focused stream 18, 19, 20 of the flowable medium (31) being supplied. After the flowable medium leaves the aperture 17 at the top, the streams of flowable medium widen as shown in FIG. 4 by the curved arrows 35. The second part of the flowable medium leaving the aperture 17 at the top, which is allowed to leave in the space 32 around the aperture 17, is shown by the arrows 35. This takes place not least because of the pressure differential between the high pressure in the supply line 16 and the atmospheric pressure in the space 32 around the aperture 17 of the container 1.

The arrow 36 curved to the right further above the aperture 17, shows the first part of the flowable medium leaving the surroundings of the aperture 17 and the space 32, which is suctioned in the venting line 22 in the direction of the arrow 37.

The suctioning in the venting line 22 as the suctioning means is done by means of an annular gap 38 which outwardly surrounds the inlet nozzle 30 at a distance. In this way a suction space 39 is formed, with which the venting line 22 is in direct connection via the passage 40.

The inlet nozzle 30 widens towards the outflow side and opens out into a high pressure chamber 41, which is connected to the interior of the supply line 16.

The planar surface 27 right at the bottom, facing the aperture 17 of the packaging container 1, has, outside the annular gap 28, a radius fitting the preferably larger area planar surface 27. The flowable medium flowing in centrally from above in the direction 31 produces a dynamic pressure above atmospheric pressure in the packaging container 1 within the briefest time, so that the flow pattern described, according to the flow arrows 35 and 36, is produced.

In order to facilitate a focused, central introduction of a stream of flowable medium along the central lines 28, 29, the lower front end of the inlet nozzle 30 visibly projects by a distance out of the planar surface 27 (outside the annular gap 38). It must be ensured that between the upper edge 26 of the respective container 1 and the furthest forward lowest surface of the inlet nozzle 30, to the extent that this projects from the surface 27, is always at a large enough distance for the packaging container 1 can be moved under the outlet 15 during intermittent further movement by the linear conveyor 8 without disturbance.

What is claimed is:

1. A method for sterilizing, filling and closing at least one packaging container open on one side, comprising the steps of:

a) transporting a packaging container along a time-controlled processing line;

b) sterilizing the packaging container with a sterilizing agent, wherein the sterilizing agent is blown under a pressure above atmospheric pressure through an aperture of the packaging container into the packaging container, the sterilizing agent entering the packaging container flowing up to, and including, a central portion or a base or an area in between the central portion and the base of the packaging container, being deflected in an interior of the packaging container towards the aperture of the packaging container, and being removed and pressed out of the container whereby, a first exiting portion of the sterilizing agent is formed and removed from an area surrounding the aperture of the container whereby the first exiting portion is removed out of the aperture of the container, and a second exiting portion of the sterilizing agent exits through a space proximate the aperture of the packaging container;

c) drying the packaging container with sterile air;

d) filling the packaging container with a sterile product; and e) applying a sterile closure to the packaging container.

2. A method according to claim 1, wherein during sterilizing, the first exiting portion of the sterilizing agent being removed out of the aperture of the packaging container surrounds a narrowly focused stream of the sterile product being supplied, and after leaving the aperture, partially widens out radially.

3. A method according to claim 1, wherein the packaging container is moved freely below a fluid supply means in a horizontal direction.

4. A method according to claim 1, wherein the packaging container is transported in a horizontal direction with its aperture facing upwards.

5. A method according to claim 1, wherein prior to introduction of the sterilizing agent into the packaging container, hot air is introduced for pre-warming.

6. A method according to claim 1, wherein the sterilizing agent is at least hydrogen peroxide ($H_2O_2$), and the packaging container is shaped as a bottle.

7. A method according to claim 1, wherein the sterilizing agent is at least hydrogen peroxide ($H_2O_2$).

8. A method according to claim 1, wherein the packaging container is shaped as a bottle.

* * * * *